US005714313A

United States Patent [19]

Garfinkel et al.

[11] Patent Number: 5,714,313
[45] Date of Patent: Feb. 3, 1998

[54] SIMPLE METHOD FOR DETECTING INHIBITORS OF RETROVIRAL REPLICATION

[75] Inventors: David J. Garfinkel; Dwight V. Nissley, both of Frederick, Md.; Joan M. Curcio, Albany, N.Y.; Jeffrey N. Strathern, Frederick, Md.

[73] Assignee: United States of America as represented by the Department of Health and Human Services, Washington, D.C.

[21] Appl. No.: 449,207

[22] Filed: May 24, 1995

Related U.S. Application Data

[63] Continuation-in-part of Ser. No. 102,854, Aug. 6, 1993, Pat. No. 5,462,873, which is a continuation of Ser. No. 668,865, Mar. 13, 1991, abandoned.

[51] Int. Cl.$^6$ .............................. C12Q 1/70; C12N 1/19; C12N 15/81
[52] U.S. Cl. .............................. 435/5; 435/6; 435/240.2; 435/254.2; 435/320.1
[58] Field of Search .............................. 435/5, 6, 240.2, 435/320.1, 172.1, 172.3, 254.2

[56] References Cited

PUBLICATIONS

Heidmann et al., "Retransposition of a Mouse IAP Sequence Tagged With an Indicator Gene" *Cell* 84: 159–170 (Jan. 1991).
Garfinkel, D. et al., "Transposon Tagging Using Ty Elements in Yeast," *Genetics* 120: 95–108 (Sep. 1988).
Boeke, J.D. et al., "A General Method for the Chromosomal Amplification of Genes in Yeast" *Science* 239:280–282 (Jan. 1988).
Boeke, J.D. et al., "Ty Elements Transpose Through an RNA Intermediate" *Cell* 40:491–500 (Mar. 1985).
Heidmann, T. et al., "An Indicator Gene to Demonstrate Intracellular Transposition of Defective Retroviruses," *Proc. Natl. Acad. Sci. USA* 85:2219–2223 (Apr. 1988).
Kim and Loeb, "Human Immunodeficiency Virus Reverse Transcriptase Substitutes for DNA Polymerase I in *Escherichia coli*," *Proc. Natl. Acad. Sci. USA* 92:684–688, Jan. 1995.
Curcio and Garfinkel, "Single–Step Selection for TY1 Element Retrotransposition," *Proc. Natl. Acad. Sci. USA* 88:936–940 (Feb. 1991).
Dombroski et al., "An in Vivo Assay for the Reverse Transcriptase of Human Retrotransposon L1 in *Saccharomyces cerevisiae*," *Molecular and Cellular Biology* 14(7):4485–4492 (Jul. 1994).
Sharon et al., "Efficient Homologous Recombination of Ty1 Element cDNA when Intergration is blocked," *Molecular and Cellular Biology* 14(10):6540–6551 (Oct. 1994).
Derr and Strathern, "A Role for Reverse Transcripts in Gene Conversion," *Nature* 361:170–173 (Jan. 14, 1993).
Derr et al., "RNA–Mediated Recombination in *S. cerevisiae*," *Cell* 67:355–364 (Oct. 18, 1991).

*Primary Examiner*—David Guzo
*Attorney, Agent, or Firm*—Needle & Rosenberg, PC

[57] ABSTRACT

The present invention relates, in general, to a DNA segment. In particular, the present invention relates to a DNA segment comprising a selectable marker gene, a DNA segment comprising a selectable marker gene inserted into a retrotransposon, cells containing these DNA segments, and methods of using these DNA segments and cells. The present invention further relates to a vector comprising a selectable marker gene inserted into a retrotransposon, wherein the retrotransposon comprises a retroviral reverse transcriptase/RNase H gene domain and wherein the selectable marker gene contains an intron inserted into a coding sequence of the marker gene and the intron is in antisense orientation relative to transcription of the marker gene and in sense orientation relative to transcription of the retrotransposon.

21 Claims, 9 Drawing Sheets

− Histidine     + Histidine

FIG.6A
−Histidine, +Hydroxyurea, −Uracil
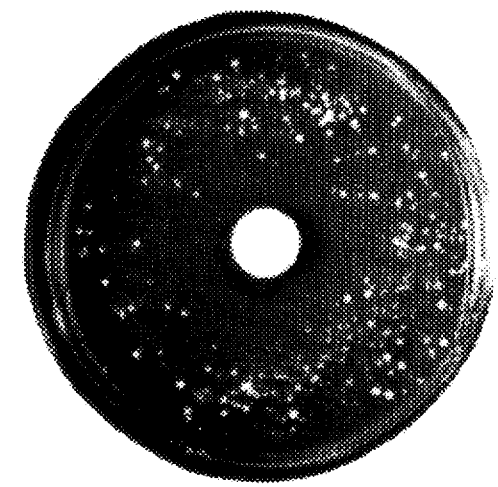
FIG.6B
+Histidine, +Hydroxyurea, −Uracil
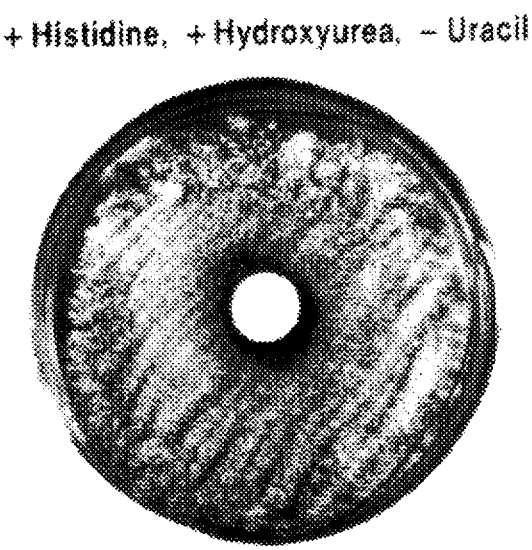
−Histidine, −Hydroxyurea, −Uracil
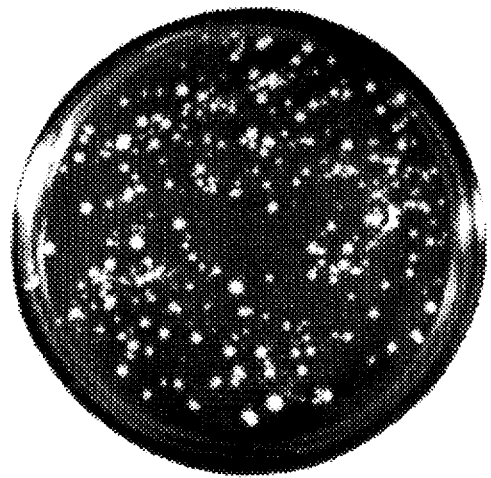
FIG.6C ATTCACCTGATTGCAGCTGTAAAAGCAGTAAAA
IleHisLeuIleAlaAlaValLysAlaValLys ATTCACCTGATTGCAGCTCTAAAAGCAGTACCCATTAGCCCTATT
IleHisLeuIleAlaAlaLeuLysAlaValProIleSerProIle
HIV-RT,RH

SIMPLE METHOD FOR DETECTING INHIBITORS OF RETROVIRAL REPLICATION

This is a continuation-in-part of application U.S. Ser. No. 08/102,854, filed Aug. 6, 1993, issued as U.S. Pat. No. 5,462,873, which is a continuation of U.S. Ser. No. 07/668,865, filed Mar. 13, 1991, abandoned.

BACKGROUND OF THE INVENTION

1. Field of the Invention

The present invention relates, in general, to a DNA segment. In particular, the present invention relates to a DNA segment comprising a selectable marker gene, a DNA segment comprising a selectable marker gene inserted into a retrotransposon, cells containing these DNA segments, and methods of using these DNA segments.

2. Background Art

Ty elements of *Saccharomyces cerevisae* are retrotransposons that are similar to retroviral proviruses (Bocke, J. D. (1989)) in *Mobile DNA*, eds., Berg, D. E. & Howe, M. M. (Am. Soc. Microbiol, Washington), pp. 335–374). Retrotransposition is a replicative process involving reverse transcription of Ty mRNA and integration of Ty cDNA into the genome (Boeke et at. *Cell* (1985) 40:491–500). Ty1 elements are the most common insertional mutagen and comprise the most numerous family of the four Ty element classes, with about 25–30 copies of Ty1 per haploid genome (Cameron, et al. *Cell* (1979) 16:739–751; Curcio, M. J. et al. *Mol. Gen. Genet.* (1990) 220:213–221). Despite the fact that Ty1 RNA accounts for 1% of total yeast KNA (Curcio, M. J. et al. *Mol. Gen. Genet.* (1990) 220:213–221), the rate of transposition is quite low (Giroux, C. N., et al. *Mol. Cell. Biol.* (1988) 8:978–981; Boeke, J. D. et al. *Mol. Cell. Biol.* (1986) 6:3575–3581; Paquin, C. E. et al. *Mol. Cell. Biol.* (1986) 4:70–79). Several modulators of transposition have been described. For example, Ty transposition is stimulated at temperatures below 30° C. (Paquin, C. E., et al. *Science* 1984) 226:53–55, by exposure of the cells to ultraviolet irradiation or 4-nitroquinoline 1-oxide (Bradshaw, V. A., et al. *Mol. Gen. Genet.* (1988) 218:465–474), or in a *rad6* mutant background (Picologlou, et al. *Mol. Cell. Biol.* (1990) 10:1017–1022. Mutations in the SPT3 gene alter the initiation of Ty1 transcription (Winston, et al. *Cell* (1984) 39:675–682) and abolish retrotransposition of chromosomal Ty1 elements (Boeke, J. D. et al. *Mol. Cell. Biol.* (1986) 6:3575–3581). These modulators of retrotransposition were identified by their effect on the frequency of Ty insertions into specific loci and not into the genome as a whole. As a result, it can be difficult to determine whether the modulators alter Ty elements directly or the target locus (Picologlou, et al. *Mol. Cell. Biol.* (1990) 10:1017–1022.

A tremendous induction in the rate of Ty1 transposition is achieved by expressing an active Ty element, Ty1-H3, from the inducible GAL1 promoter (Boeke et al. *Cell* (1985) 40:491–500). The pGTy1-H3 element has been marked with selectable genes such as a bacterial gene for neomycin resistance (Boeke, et al. *Science* (1988) 239:280–282) and the yeast HIS3 gene (Garfinkel, et al. *Genetics* (1988) 120:95–108). Phenotypic detection of retrotransposition events in the transposition-induction system requires loss of the pGTy plasmid. In addition, transposition of the marked Ty1 element can only be detected when it is induced to a level that exceeds the rate of homologous recombination among Ty elements (Roeder, et al. *Proc. Natl. Acad. Sci. USA* (1982) 79:5621–5625; Roeder, et al. *Mol. Cell. Biol.* (1984) 4:703–711).

Ty RNA is packaged into virus-like particles (VLPs) that are composed of Ty proteins. Ty elements contain two overlapping genes, TYA and TYB, that are equivalent to retroviral gag and pol. Ty element Gag (TYA) and Gag-Pol (TYA-TYB) polyproteins are cleaved by a Ty-encoded protease (PR) into mature proteins within the VLP. Among these are the mature capsid protein TYA, derived from a precursor protein and PR, integrase (IN), and reverse transcriptase (RT)/RNase H (RH), derived from TYA-TYB polyprotein. (Garfinkel, D. J., *The Retroviridae*, Plenum Press NY, p. 107–158 (1992).

Retroviruses and retrotransposons replicate through an RNA intermediate as part of their life cycle. All retroelements, which include retroviruses and retrotransposons, encode a reverse transcriptase that is necessary for replication. The reverse transcriptase has several enzymatic activities that are used during replication of these elements. First, the enzyme is responsible for synthesizing a DNA copy of the RNA genome. Since this entails using the RNA template for synthesis of a DNA copy, the name reverse transcriptase has been coined. The enzyme additionally has a ribonuclease H activity that degrades the RNA genome after a single-stranded DNA copy of it has been made. The enzyme also has a DNA-dependent DNA polymerase activity that is responsible for synthesizing a completely double-stranded DNA molecule after the genomic RNA has been removed.

The his3-AI indicator gene has been used to detect pseudogene formation in yeast (Derr, Strathern and Garfinkel, *Cell* 67 (1991) 355–364; Derr and Strathern, *Nature* 361 (1993)170–173 and has been used in a two plasmid system to assess activity of the reverse transcriptase of a human L1 retrotransposon in yeast (Dombroski, et al. *Mol. Cell Biol.* 14 (1994) 4485–4492. In this L1 two-plasmid system, however, the reporter gene is on one plasmid while a large fragment including the L1 reverse transcriptase gene is inserted into a second plasmid having a Ty element deleted in TyB for the Ty integrase and deleted for Ty RT/RH. Recently, Kim and Leob, *Proc. Natl. Acad. Sci.* 92 (1995) 684–688, have developed a bioassay that utilizes the DNA-dependent DNA polymerase of HIV-1 RT/RH in *Escherichia coli.* However, since DNA-dependent DNA polymerases are found in all cells, the inhibitors that are identified by a DNA-dependent DNA polymerase-based assay may also be toxic to cells and, therefore, complicate the identification of useful lead compounds.

Current methods for assays for drugs affecting HIV reverse transcriptase require either (1) test tube methods, which can give different results for a compound by varying reaction conditions, and (2) growth of live HIV virus, which requires costly BL3 laboratories and poses health risks to workers.

Therefore, there is a strong need for assays for inhibitors of reverse transcriptases, thus providing simpler, safer, and less expensive assays for antiviral drugs against viruses that utilize reverse transcriptase, such as HIV-1, HIV-2, simian immunodeficiency virus, arian immunodeficiency virus, bovine immunodeficiency virus, feline immunodeficiency virus, or equine infectious anemia virus. The present invention satisfies this need by providing an assay that detects inhibitors of reverse transcriptase/RNase H activity by a simple, inexpensive method that can readily be performed with minimal resources. Additionally, this assay allows one to directly assay the activity of the specific virus which is of relevance.

SUMMARY OF THE INVENTION

It is a general object of this invention to provide a DNA segment.

It is a specific object of this invention to provide a DNA segment comprising a selectable marker gene.

It is another object of the invention to provide a DNA segment comprising a selectable marker gene inserted into a retrotransposon.

It is a further object of the invention to provide a cell that contains the above mentioned DNA segments.

It is yet another object of the invention to provide a method of selecting cells wherein retrotransposition has occurred.

It is a further object of the invention to provide a method of detecting a compound capable of inhibiting retroviral replication or retrotransposition.

It is another object of the invention to provide a method of selecting a mutant retrotransposon that is resistant to a compound capable of inhibiting retroviral replication or retrotransposition.

Further objects and advantages of the present invention will be clear from the description that follows.

In one embodiment, the present invention relates to a DNA segment comprising a selectable marker gene containing an intron inserted into a translatable sequence coding for the marker gene wherein the intron is present in an antisense orientation relative to transcription of the marker gene.

In another embodiment, the present invention relates to a DNA segment comprising a selectable marker gene inserted into a retrotransposon wherein the marker gene contains an intron inserted into a translatable sequence coding for the marker gene and the intron is in an antisense orientation relative to transcription of the marker gene and in a sense orientation relative to transcription of the retrotransposon.

In a further embodiment, the present invention relates to cells that contain the above mentioned DNA segments.

In another embodiment, the present invention relates to a method of selecting cells wherein retrotransposition of the above mentioned retrotransposon has occurred comprising:

(1) placing the cells onto selectable media,
(2) culturing the cells, and
(3) selecting for colonies of the cells which grow.

In another embodiment, the present invention relates to a method of detecting a compound capable of inhibiting retroviral replication or retrotransposition in the above mentioned cells comprising:

(1) placing the cells onto selectable media,
(2) exposing the cells to the compound,
(3) culturing the cells, and
(4) determining if growth of the cells is inhibited.

In another embodiment, the present invention relates to a method of selecting a mutant retrotransposon that is resistant to a compound capable of inhibiting retroviral replication or retrotransposition in the above-described cells comprising:

(1) placing the cells onto selectable media,
(2) exposing the cells to the compound,
(3) culturing the cells, and
(4) selecting cells whose growth is not inhibited by the compound.

The present invention also provides a vector comprising a selectable marker gene inserted into a retrotransposon, wherein the retrotransposon comprises a retroviral reverse transcriptase/RNase H gene domain and wherein the selectable marker gene contains an intron inserted into a coding sequence of the marker gene and the intron is in antisense orientation relative to transcription of the marker gene and in sense orientation relative to transcription of the retrotransposon.

The present invention further provides cells that contain the above-described vector. The instant invention further provides a method of screening for a compound for the ability to inhibit retroviral replication comprising (a) contacting with the compound a cell into which is transferred a vector comprising a selectable marker gene inserted into a retrotransposon, wherein the retrotransposon comprises a retroviral reverse transcriptase/RNase H gene domain and wherein the selectable marker gene contains an intron inserted into a coding sequence of the marker gene and the intron is in antisense orientation relative to transcription of the marker gene and in sense orientation relative to transcription of the retrotransposon, in selective media, (b) culturing the cell and (c) detecting inhibition of growth of the cell, a compound that inhibits growth of the cell being a compound that inhibits retroviral replication.

The present invention additionally provides a method of screening for a compound for the ability to inhibit reverse transcriptase comprising (a) contacting with the compound a cell into which is transferred a vector comprising a selectable marker gene inserted into a retrotransposon, wherein the retrotransposon comprises a retroviral reverse transcriptase/RNase H gene domain and wherein the selectable marker gene contains an intron inserted into a coding sequence of the marker gene and the intron is in antisense orientation relative to transcription of the marker gene and in sense orientation relative to transcription of the retrotransposon, (b) culturing the cell, in selective media and (c) detecting inhibition of growth of the cell, a compound that inhibits growth of the cell being a compound that inhibits reverse transcriptase.

Also provided by the present invention is a method of screening for a compound for the ability to inhibit retroviral replication comprising (a) culturing a cell that is transformed with a vector comprising a DNA segment comprising a selectable marker gene inserted into a retrotransposon wherein the selectable marker gene contains an intron inserted into a coding sequence of the gene and the intron is present in an antisense orientation relative to transcription of the marker gene and in a sense orientation relative to transcription of the retrotransposon, in selective media, (b) contacting the cell with the compound, and (c) detecting inhibition of growth of the cell, a compound that inhibits growth of the cell being a compound that inhibits retroviral replication.

The present invention further provides a method of screening for a compound for the ability to inhibit retrotransposition comprising (a) culturing a cell that is transformed with a vector comprising a DNA segment comprising a selectable marker gene inserted into a retrotransposon wherein the selectable marker gene contains an intron inserted into a coding sequence of the gene and the intron is present in an antisense orientation relative to transcription of the marker gene and in a sense orientation relative to transcription of the retrotransposon, in selective media, (b) contacting the cell with the compound, and (c) detecting inhibition of growth of the cell, a compound that inhibits growth of the cell being a compound that inhibits retrotransposition.

BRIEF DESCRIPTION OF THE DRAWINGS

FIG. 6. (Parts A–C) Detection of Reverse Transcriptase/RNase H inhibitors. Cells containing an spt3 mutation and HART21 were spread onto SC-uracil galactose plates containing 100 microliters of a 2M hydroxyurea solution (200 µm) spotted onto a sterile filter placed in the center of the plate. After incubation at 20° C. for five days, the plates were replicaplated to the following media, incubated at 30° C. and photographed: Panel A, SC-histidine+hydroxyurea-uracil plate to detect inhibition of His$^+$ formation by continued presence of hydroxyurea; Panel B, SC+histidine+hydroxyurea-uracil plate to detect general inhibition of growth by hydroxyurea; Panel C, SC-histidine-hydroxyurea-uracil to show the level of His$^+$ colony formation in the absence of hydroxyurea.

DETAILED DESCRIPTION OF THE INVENTION

Figure 1A:
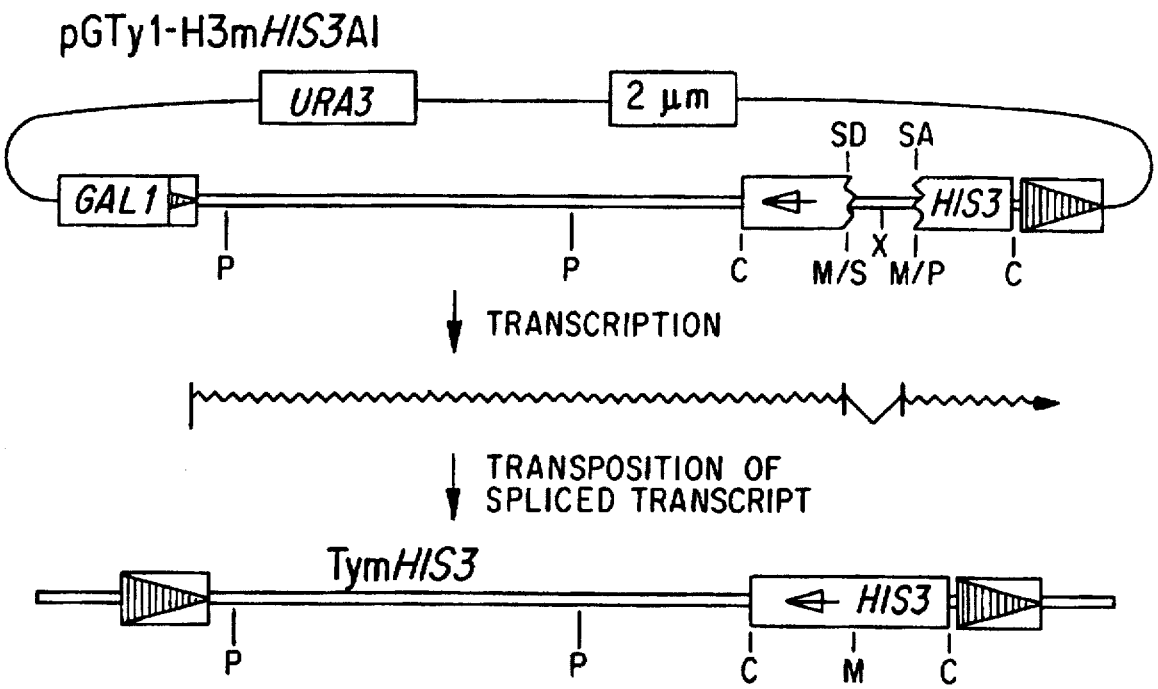
FIG. 1. (Parts A–C). Genetically marked derivatives of plasmid pGTy1-H3. (A) Structure of plasmid pGTy1-H3mHIS3AI. The boxed arrow heads represent the Ty1 long terminal repeats and the direction of Ty1 transcription. The shaded box represents the yeast HIS3 gene and the enclosed arrow indicates its direction of transcription. AI sequences, represented by the broken line, are in the antisense orientation relative to the HIS3 gene but in the sense orientation relative to Ty1-H3. The Ty1 -H3mHIS3AI transcript is represented by the wavy line. Splicing is indicated by vertical lines in the transcript. TymHIS3 is the spliced and transposed copy of the marked element. (B) Structure of the GAL1-Ty1 fusion element contained in plasmid pGTy1-H3HIS3mAI. In this plasmid, the HIS3AI gene is transcribed in the same direction as the Ty1 element, and the intron, which is in the antisense orientation relative to both Ty1-H3 and HIS3 transcription, is unspliceable. (C) The element contained on pGTy1-H3mHIS3. The abbreviations used are: GAL1, yeast GAL1 promoter; SD, splice donor; SA, splice acceptor; URA3, yeast URA3 gene; 2 µm, yeast 2µm origin of replication; P, Pvu II; C, Cla I; X, XbaI; M, Msc 1; M/S, Msc I/SnaBI hybrid sites; M/P, Msc I/Pvu II hybrid sites.

The present invention may be understood more readily by reference to the following detailed description of specific embodiments and the Examples included therein.

The present invention relates to DNA segments comprising a selectable marker gene or a selectable marker gene inserted into a retrotransposon.

More specifically, the present invention relates to DNA segments comprising a selectable marker gene wherein the selectable marker gene contains an intron inserted into a translatable sequence coding for the marker gene wherein the intron is present in an antisense orientation relative to transcription of the marker gene. In one preferred embodiment, the selectable marker gene is HIS3 and contains the above-described intron (for example—HIS3AI.

In another embodiment, the present invention relates to a DNA segment comprising a selectable marker gene inserted into a retrotransposon wherein the marker gene contains an intron inserted into a translatable sequence coding for the marker gene and the intron is in an antisense orientation relative to transcription of the marker gene and in a sense orientation relative to transcription of the retrotransposon. In one preferred embodiment, the intron is an artificial intron (preferably, a yeast artificial intron or more specifically, a 104-base-pair artificial yeast intron contained on a PvuII-SnaB1 fragment). In another preferred embodiment, the selectable marker gene is HIS3 and contains the above-described intron (examples include: HIS3AI, Ty1-

H3mHIS3A1, and pGTy1-H3mHIS3A1). In a further preferred embodiment, the retrotransposon is a yeast retrotransposon (for example—Ty1).

In a further embodiment, the present invention relates to a cell containing the above described DNA segments (suitable host cells include procaryotes (such as bacteria) and both lower eucaryotes (for example yeast) and higher eucaryotes (for example, mammalian cells). Introduction of the DNA segment into the host cell can be affected using methods known in the art.

In another embodiment, the present invention relates to a method of selecting the above described cells wherein retrotransposition of the retrotransposon has occurred comprising:

(1) placing the cells onto selectable media,
(2) culturing the cells, and
(3) selecting for colonies of the cells which grow.

This method has several advantages over other transposition-detection systems used (Boeke et al. *Cell* (1985) 40:491–500; Boeke, et al. *Science* (1988) 239:280–282; Garfinkel, et al. *Genetics* (1988) 120:95–108). Since the reporter gene is only phenotypically activated in retrotransposed copies of the marked element, transposition can be scored in the presence of the original marked element. Moreover, selection for the transposition of chromosomal elements can be performed in the absence of insertions into specifics targets. This feature will be extremely useful in identifying genes that modulate Ty transposition. An advantage of the HIS3AI reporter gene is that splicing of the reverse transcript results in the creation of an Msc I site, allowing presence of the exact splice junction to be confirmed at the nucleotide level in a Southern blot. Additionally, other rearrangements that phenotypically activate HIS3AI occur at a very low frequency.

In a further embodiment, the present invention relates to a method of detecting a compound (for example—hydroxyurea) capable of inhibiting retroviral replication or retrotransposition in the above described cells comprising:

(1) placing the cells onto selectable media,
(2) exposing the cells to said compound,
(3) culturing the cells, and
(4) determining if growth of the cells is inhibited.

The above described method can be also used to detect compounds that affect splicing. Reagents of this type could be identified in a secondary screen.

In a further embodiment, the present invention relates to a method of selecting a mutant retrotransposon that is resistant to a compound capable of inhibiting retroviral replication or retrotransposition in the above described cells comprising:

(1) placing the cells onto selectable media,
(2) exposing the cells to the compound,
(3) culturing the cells, and
(4) selecting cells whose growth is not inhibited by the compound.

The present invention further provides a vector comprising a selectable marker gene inserted into a retrotransposon, wherein the retrotransposon comprises a retroviral reverse transcriptase/RNase H gene domain and wherein the selectable marker gene contains an intron inserted into a coding sequence of the marker gene and the intron is in antisense orientation relative to transcription of the marker gene and in sense orientation relative to transcription of the retrotransposon. This vector thus provides an assay for detecting inhibitors of certain retrotranspositional events. For example, inhibitors of any of the activities of retroviral reverse transcriptase can be detected. Additionally, inhibitors of the Ty protease or any other substituted protease, can be detected, as can inhibitors of cellular genes involved in homologous recombination events. Once a lead compound has been identified by the present method, its specific mode of inhibition can be determined by using known methods for detection of specific biochemical activities. The present method, however, provides an inexpensive, easy assay to screen compounds initially. Further, because of the precision with which the selected retroviral RT/RH can be substituted into the present vector, compounds very specific for inhibiting the selected RT/RH can be detected.

As used in the specification and in the claims, "a" or "an" can mean one or more, depending upon the context in which it is used.

The inventive vector provides a functional hybrid retroelement, utilizing, for example, the yeast Ty1, containing a RT/RH domain from a selected retrovirus in place of the retroelement's original RT/RH domain. The vector further comprises an indicator (marker) gene having an intron inserted into a coding sequence of the marker gene in antisense orientation relative to transcription of the marker gene and in sense orientation relative to transcription of the retrotransposon. Therefore, activity of a selected retroviral RT/RH, such as HIV-1 RT/RH, can be monitored using inexpensive and simple microbiological manipulations in yeast.

Figure 5A:
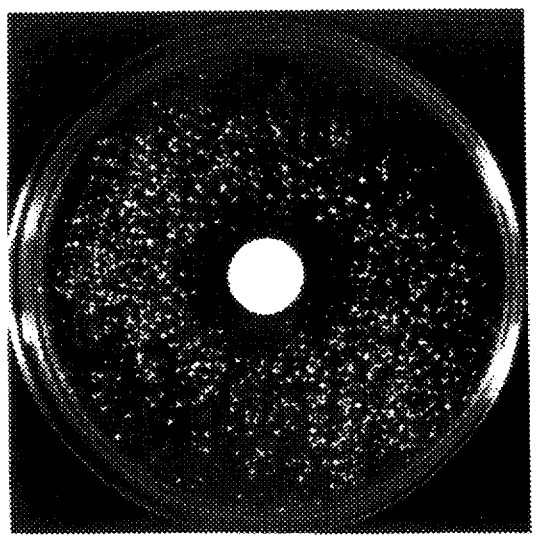
FIG. 5. (Parts A–B) Hydroxyurea inhibits Ty transposition. Approximately 1×10$^7$ cells harboring the plasmid pGTy1-H3mHISAI were plated onto growth media containing galactose and lacking uracil. The plate in panel A lacks histidine, which only supports growth of cells that have undergone transposition of the Ty1-H3mHISAI element; the plate in panel B contains histidine, which supports the growth of all cells. Filters saturated with a 2M solution of hydroxyurea were added to the plates. Plates were incubated for 3 days at 30° C. and then photographed. The histidine-dependent zone of inhibition indicates that hydroxyurea inhibits Ty transposition but not growth of yeast cells.
Figure 5B:
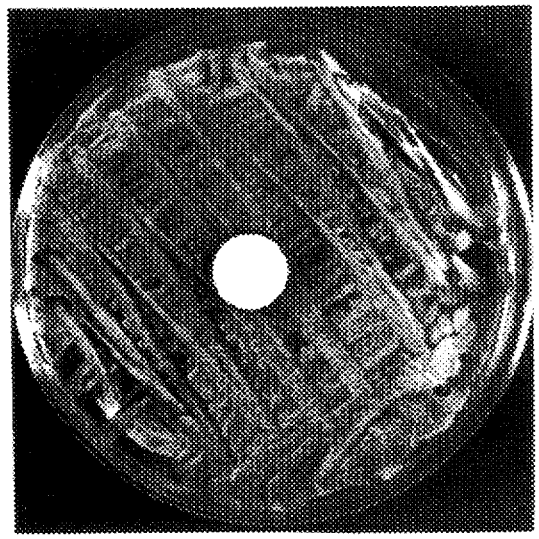

One example vector, HART21, is an improvement over Ty1 his3-AI for use in detecting retroviral inhibitors because HART21 contains the HIV-1 RT/RH coding domain in place of Ty1 RT/RH. Therefore it provides a direct assay of the retroviral RT/RH activity. The development of HART21 provides an assay that can be readily adapted for use with any retroviurs of interest by substituting the RT/RH gene of the retrovirus of interest into this vector, replacing the HIV-1 RT/RH, and by maintaining an open reading frame. Additionally mutations within the HIV-1, or any other retroviral, RT/RH gene can now readily be made by standard methods. The present method demonstrates that the process of forming His+ cells is dependent on HIV-1 RT using the HART21 vector (Table 5). The present method also uses HART21 to exemplify a bioassay to identify an inhibitor of HIV-1 RT/RH (FIG. 6). Furthermore, the HART21 assay demands that HIV-1 RT/RH functions as a RT and a RH, which are biochemical activities used by many retrotransposons and all retroviruses for replication (FIG. 5).

The His+ events obtained with HART21 and any present vector substituting different retroviral RT/RH domains into the retrotransposon can result, instead of from retrotransposition, from a related process termed cDNA-mediated recombination, a homologous recombination process. cDNA-mediated recombination predominates when reverse transcription products do not undergo transpositional integration catalyzed by the Ty1-encoded enzyme integrase. The cDNA product undergoes homologous recombination with endogenous Ty elements residing in the yeast genome. The His+ cDNA recombination events are completely dependent on functional RT/RH and, therefore, serve as a faithful biological indicator of retroviral RT/RH activities in yeast (FIG. 5). Additionally, a His+ event requires the RT to act as an RNA-dependent DNA polymerase and ribonuclease H, activities that are unique to this type of enzyme. Therefore, the present assay to detect inhibitors of RT/RH provides a useful screen for compounds for drug intervention in therapy against retroviral infection.

That a homologous recombination event, rather than a retrotransposition event, occurs with any of the present retroviral RT/RH vectors to produce a His⁺ phenotype can be tested by any of several standard methods, several of which are described herein. For example, the general site of insertion of the reverse transcription product, i.e., into endogenous Ty elements in the host chromosome or into the Ty element on the plasmid, can be detected by tracking the stability of the markers. Transposition events do not result in a significant amount of insertion of the reverse transcription product into the plasmid DNA in the cell, whereas homologous recombination results in insertion of the product into both the chromosome and the plasmid by virtue of the presence of Ty elements in both. Therefore, the marker on the reverse transcription product, if homologous recombination occurs, becomes genetically linked with markers on the plasmid, which can be readily detected by standard means.

Alternatively, the vectors can be transferred into a mutant yeast strain in which homologous recombination is inhibited by virtue of yeast cellular gene mutation(s). In these cells, if His⁺ events are occurring at the same level as in cells that are wild type for homologous recombination, His⁺ events are occurring by a non-homologous recombination event, i.e., by retrotransposition. If, in these cells, His⁺ events occur at a statistically significantly lower level (at approximately background level), then the His⁺ events are occurring by homologous recombination.

Furthermore, transposition or homologous recombination can be determined by analysis of the physical nucleic acid structures involved. For example, retrotransposition into chromosomal DNA produces a distinctive characteristic structure which can be detected by standard methods such as polymerase chain reaction (PCR) (Liebman, S. W., Newnam, G. *Genetics* 133 (1993) 499–508), or Southern blot analysis (Boeke, et al., *Cell* 40 (1985) 491–500). Homologous recombination occurs by complex events, and thus it produces complex structural products which can also be detected by standard methods such as PCR or Southern blot analysis (Derr, et al., *Cell* 67:355–364 (1991); Sharon, G., Burkett, T. J. and Garfinkel, D. J., *Mol. Cell. Biol.* 14:6540–6551 (1994)).

The retrotransposon utilized in the present vector can be any selected retrotransposon, such as a *Saccharomyces cerevesiae* Ty element or a *Schizosaccharomyces pombe* Tf element. A preferable retrotransposon is the budding yeast Ty1 retrotransposon. The term "retrotransposon" as used in the claims includes that substitutions, mutations, additions, etc. can be made to a selected existing retrotransposon. The retrotransposon includes an RT/RH coding sequence, though the functioning of the RT/RH can be altered or destroyed in RT/RH encoded by the vector. Additionally, the retrotransposon preferably includes, e.g., an integrase/transposase coding sequence, a protease coding sequence, terminal repeat sequences, promoter sequence(s) and a sequence encoding a Gag-like protein. Furthermore, the retrotransposon preferably has a Ty protease cleavage site encoded at the natural site of cleavage (between the integrase and the reverse transcriptase) in the polyprotein. This cleavage site preferably provides precise cleavage so that the first amino acid of the RT/RH protein is correct, as exemplified herein.

As used herein, "a retroviral reverse transcriptase/RNase H gene domain" and "a RT/RH" are used interchangeably and refer to a nucleic acid encoding a reverse transcriptase. Reverse transcriptase, which is encoded by all retroviruses and retrotransposons, has several activities, including a RNA-dependent DNA polymerase activity, a RNase H activity and a DNA-dependent DNA polymerase activity. A RT/RH as used herein can include a nucleic acid encoding RT/RH derived from any retrovirus or retrotransposon as well as such nucleic acids harboring mutations. The RT/RH used in the present vectors can be derived from, for example, HIV-1, HIV-2, SIV, avian immunodeficiency virus, bovine immunodeficiency virus, feline immunodeficiency virus or equine infectious anemic virus.

The present vector allows the construction of a vector that can produce a precise, accurate RT/RH protein. Thus assays for inhibitors of the RT/RH in the vector can detect drugs that are very specific for the mature RT/RH produced in vivo, for example, during an infection.

As used in the claims, an "inducible promoter" can include any of many inducible promoters known in the art. It is preferable to select the promoter to be compatible with the cell system to be used for a screening. For example, the GAL1 promoter is readily inducible in a yeast system.

Any desirable selectable marker gene can be utilized in the present vectors. Choice of a marker gene can be based upon the cell system to be used and ease of performing the selection for cells harboring the marker gene. For example, yeast cells are readily grown on media selective for His⁺ cells, making the yeast HIS3 gene a useful marker.

The intron inserted into the marker gene can be any functional intron, such as an intron derived from a naturally-occurring sequence or an artificial intron such as the yeast artificial intron, as known in the art.

The present invention includes cells transformed with the present vectors. By a cell "transformed" with a vector of the present invention, as used in the claims, is meant a cell into which the vector is transferred by any means, such as by infection, conjugation, transformation, transfection, electroporation, microinjection, calcium chloride precipitation or liposome-mediated transfer.

The present invention further provides a method of screening a compound for the ability to inhibit retroviral replication comprising contacting a cell transformed with a vector comprising a selectable marker gene inserted into a retrotransposon wherein the retrotransposon comprises HIV-1 RT/RH gene and wherein the marker gene contains an intron inserted into a coding sequence of the marker gene and the intron is in antisense orientation relative to transcription of the marker gene and in sense orientation relative to transcription of the retrotransposon. In the present assays, the culturing and contacting steps can be performed as exemplified herein or the compound can be added simultaneously with culturing. The assay will not be helpful, however, if the compound is added after His⁺ events have occurred. Time periods for culturing the cells will vary according to growth conditions and the particular cell used, and can readily be determined using controls. By "inhibition" of growth of a cell is included any decrease in growth as compared to cells that are not contacted with the screened compound, and relative inhibition can be detected. The selective media is selected according to the selectable marker gene having the intron inserted in antisense orientation in the vector. Inhibitors of replication of any desired retrovirus can be screened by this method, such as HIV-1, HIV-2, SIV, and other retroviruses such as those mentioned herein.

The present invention also provides a method of screening for a compound for the ability to inhibit reverse transcriptase comprising (a) contacting a cell transformed with a vector comprising a selectable marker gene inserted into a retrotransposon, wherein the retrotransposon comprises a retroviral reverse transcriptase/RNase H gene domain and wherein the selectable marker gene contains an intron inserted into a coding sequence of the marker gene and the intron is in antisense orientation relative to transcription of the marker gene and in sense orientation relative to transcription of the retrotransposon with the compound, (b) culturing the cell in selective media and (c) detecting inhibition of growth of the cell, a compound that inhibits growth of the cell being a compound that inhibits reverse transcriptase.

The present invention further provides a method of screening for a compound for inhibiting retroviral replication comprising (a) culturing a cell that is transformed with a vector comprising a DNA segment comprising a selectable marker gene inserted into a retrotransposon wherein the selectable marker gene contains an intron inserted into a coding sequence of the gene and the intron is present in an antisense orientation relative to transcription of the marker gene and in a sense orientation relative to transcription of the retrotransposon, in selective media, (b) contacting the cell with the compound, and (c) detecting inhibition of grog of the cell, a compound that inhibits growth of the cell being a compound that inhibits retroviral replication.

The present invention further provides a method of screening for a compound for inhibiting retrotransposition comprising (a) culturing a cell that is transformed with a vector comprising a DNA segment comprising a selectable marker gene inserted into a retrotransposon wherein the selectable marker gene contains an intron inserted into a coding sequence of the gene and the intron is present in an antisense orientation relative to transcription of the marker gene and in a sense orientation relative to transcription of the retrotransposon, in selective media, (b) contacting the cell with the compound, and (c) detecting inhibition of growth of the cell, a compound that inhibits growth of the cell being a compound that inhibits retrotransposition.

Statement Concerning Utility

The utility of the present invention is readily apparent from the above description. A few additional examples demonstrating such utility follow. The present invention provides a vector that allows for the monitoring of reverse transcriptase and RNAse H activity, thus providing a means to screen for compounds that inhibit reverse transcription activity, e.g., RNA-dependent DNA polymerase activity and/or RNAse H activity. These activities are unique to reverse transcriptase, and thus to viruses that utilize them. Thus this invention provides a means to screen for antiviral compounds. This assay can be used, for example, to screen for anti-HIV drugs. However, additionally, it can be used to screen for drugs for inhibiting animal retroviruses, such as simian immunodeficiency virus, avian immunodeficiency virus, bovine immunodeficiency virus, feline immunodeficiency virus, or equine infectious anemia virus. Thus it can be used to screen for drugs for treating the retroviral diseases caused by these viruses, such as feline AIDS and avian retroviral diseases. The present invention provides an easier, less expensive assay that poses much less risk to the worker performing the test than assays involving manipulation of the virus itself. Additionally, it can be performed with minimal equipment, and therefore, can be performed in very modest laboratories. Furthermore, because the present RT/RH vector allows the construction of vectors that produce the precise RT/RH made by the retrovirus from which it is derived, an assay for inhibitors of the RT/RH encoded by these vectors can detect drugs that can have specificity for the specific RT/RH. Thus, anti-RT/RH drugs that are less toxic to cells generally can be identified by this screen.

EXAMPLES

The present invention is more particularly described in the following examples which are intended as illustrative only since numerous modifications and variations therein will be apparent to those skilled in the art.

Plasmid Constructions

Figure 1B:
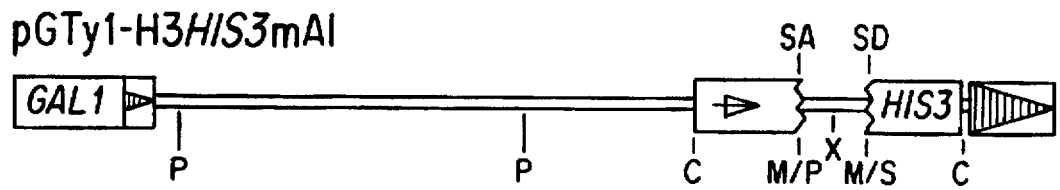
Figure 1C:
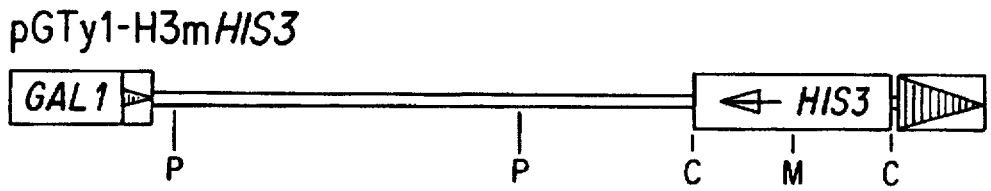

The HIS3AI indicator gene was constructed by cloning a 104-base-pair artificial yeast intron (AI), contained on a Pvu II-SnaBI fragment (Yoshimatsu, et al. *Science* (1989) 244:1346–1348), into the blunt-end Msc I site of HIS3 carried on pCLA12HIS3 (Garfinkel, et al. *Genetics* (1988) 120:95–108; Struhl, K. *Nucleic Acids. Res.* (1985) 13:8587–8601), to form pCLA12HIS3AI. The predicted intron-exon junctions were confirmed by DNA sequencing (Sanger, et al. *Proc. Natl. Acad. Sci.* (1977) 74:5463–5467. A HIS3AI Cla I fragment was cloned into the Cla I site of pGTy1-H3CLA (Garfinkel, et al. *Genetics* (1988) 120:95–108) in both orientations. The resulting plasmids have HIS3AI in either the sense or antisense orientation relative to Ty1-H3 transcription and are called pGTy1-H3mHIS3AI or pGTy1-H3HIS3mAI, respectively (FIG. 1, A and B). Plasmid pGTy1-H3mHIS3 was made by inserting the Cla I fragment of pCLAI2HIS3 into the Cla I site of pGTy1-H3CLA (FIG. 1C).

Yeast Strains and Media

The yeast strains used are GRF167 (MATα, ura3-167, his3-Δ200, GAL), and an isogenic spt3 derivative, DG789, both of which contain a complete HIS3 deletion (Boeke et al. *Cell* (1985) 40:491–500; Struhl, K. *Nucleic Acids. Res.* (1985) 13:8587–8601). Strains JC234, JC242, JC246, and JC271 are congenic derivatives of GRF167 that contain different unspliced TymHIS3AI insertions. These strains were isolated after galactose induction of plasmid pGTy1-H3mHIS3AI in strain GRF167 and subsequent segreation of the pGTy plasmid. Standard yeast media were prepared as described by Sherman et al. (Sherman, et al. *Laboratory Course Manual for the Methods in Yeast Genetics* (Cold Spring Harbor Lab., Cold Spring Harbor, N.Y.) (1986).

Transposition Efficiencies

To determine the fraction of cells that sustain a marked transposition in strains containing pGTy1-H3HIS3AI plasmids, cultures were inoculated at low densities and grown to saturation at 20° in SC-ura galactose (Sherman, et al. *Laboratory Course Manual for the Methods in Yeast Genetics* (Cold Spring Harbor Lab., Cold Spring Harbor, N.Y.) (1986)) to induce transposition or in SC-ura glucose (Sherman, et al. *Laboratory Course Manual for the Methods in Yeast Genetics* (Cold Spring Harbor Lab., Cold Spring Harbor, N.Y.) (1986)). A portion of each culture was then plated onto SC-his glucose plates (Sherman, et al. *Laboratory Course Manual for the Methods in Yeast Genetics* (Cold Spring Harbor Lab., Cold Spring Harbor, N.Y.) (1986)) and grown at 30° C. to end the transposition induction and score histidine prototrophs. The cultures were titered on YEPD plates.

Southern Blot Analysis of Transposition-Induced Strains

Strains containing pGTy plasmids were grown for 5 days at 20° C. on SC-ura galactose plates. Independent colonies were recovered and processed for Southern Blot analysis with a randomly labeled HIS3 or Ty probe as described (Curcio, M. J. et al. Mol. Gen. Genet. (1990) 220:213–221).

Analysis of Genomic TymHIS3AI Elements

Transposition rates were determined by the method of Lea, et al. J. Genet. (1949)49:264–285. Between 7 and 11 cultures inoculated with ≈200 cells were grown to saturation at 20° C. in YEPD and then plated onto SC-his glucose medium at 30° C. Three cultures of each strain were titered on YEPD plates. Northern blot analysis was performed with excess $^{32}$P-labeled HIS3, Ty1, and PYK1 RNA probes, as described (Curcio, M. J. et al. Mol. Gen. Genet. (1990) 220:213–221.

EXAMPLE 1

Construction of a Reporter Gene for Retrotransposition

A reporter gene for retrotransposition that consists of an AI interrupting the coding sequences of HIS3 was designed. The intron is a portable cassette containing all of the cis-acting sequences required for splicing without any flanking exon sequences (Yoshimatsu, et al. Science (1989) 244:1346–1348). The AI was inserted into the HIS3 coding sequence in an antisense orientation, thereby inactivating HIS3 and destroying an Msc I site. To form Ty1-H3mHIS3AI (the "m" indicates the presence of HIS3 gene sequences on the minus strand of Ty1-H3), the HIS3AI gene was placed on the minus strand of Ty1-H3, such that transcription of HIS3 AI is opposite of Ty transcription (FIG. 1A). Since the intron is in the antisense orientation relative to the HIS3 transcript, it is in the correct orientation to be precisely removed from the Ty1-H3 RNA transposition intermediate by splicing. Therefore, colonies harboring transposed TymHIS3 elements can be identified by growth on medium lacking histidine. Restoration of the Msc I site in transposed copies of TymHIS3 can be easily detected by Southern blot analysis, confirming the presence of the correct splice junction.

As a control for DNA recombination events that confer a His$^+$ phenotype, a derivative of Ty1-H3 containing HIS3AI in the same transcriptional orientation as Ty1-H3 (FIG. 1B) was constructed. The AI in this element, Ty1-H3HIS3mAI, is in an antisense orientation relative to both the Ty1 and HIS3 transcripts. (The "m" signifies the presence of AI on the minus strand of Ty1-H3.) Therefore, both the starting transposon and transposed copies of TyHIS3mAI should retain the intron and remain His$^-$ if splicing of the retrotransposition intermediate is required for recreation of a functional HIS3 gene.

EXAMPLE 2

Galactose Induction of pGTy1-H3mHIS3AI Transcription Results in High Levels of Retrotransposition To determine whether HIS3AI was an indicator of Ty retrotransposition, pGTy plasmids containing the Ty1-H3mHIS3AI or Ty1-H3HIS3mAI elements were introduced into yeast strain GRF167 and assayed for transposition (Table 1). The transformants were phenotypically His$^-$, indicating that the HIS3AI gene cannot confer a His$^+$ phenotype in the absence of Ty1-H3 transcription. Cells were grown in liquid medium containing galactose and then plated onto SC-his glucose medium to end transposition induction and select for His$^+$ colonies. After transposition induction of pGTy1-H3m-HIS3AI in isogenic SPT3 (Table 1) or spt3 strains (data not shown), almost 2% of the cells became His$^+$. Transcription of the Ty1-H3mHIS3AI element from the GAL1 promoter is required for this high frequency of His$^+$ reversion. When cells are grown on glucose, which represses pGTy transcription, His$^+$ colonies appear at a frequency more than five orders of magnitude lower. The frequency of histidine prototrophs observed upon transposition induction of cells containing pGTy1-H3HIS3mAI is also more than five orders of magnitude lower than strains harboring pGTy1-H3mHIS3AI (Table 1). Therefore, splicing is required for the generation of histidine prototrophs. Thus these data show that the pGTy1-H3mHIS3AI element yields a high level of retrotransposition events in which the HIS3 gene is recreated by splicing.

To confirm that His$^+$ revertants recovered after induction of pGTy1-H3mHIS3AI contained spliced TymHIS3 transpositions, 30 His$^+$ colonies were analyzed by Southern blot hybridization. All 30 colonies contained at least one integrated TymHIS3 element with bands predicted to be present only in precisely spliced TymHIS3 elements.

TABLE 1

Transposition induction of PGTy1-H3 marked with HIS3AI gene

| Ty marker | Carbon Source | No. His$^+$ colonies/ culture | Mean transposition efficiency |
|---|---|---|---|
| mHIS3AI | Gal | 349,604,577 | $1.7 \times 10^{-2}$ |
| mHIS3AI | Glc | 0,1,1 | $2.5 \times 10^{-8}$ |
| HIS3mAI | Gal | 1,0,1 | $3.2 \times 10^{-8}$ |

Each measurement represents the results from one of the three cultures. The total number of colony-forming units was similar within each set of cultures; the average titers are (top to bottom): $3.4 \times 10^4$, $2.7 \times 10^7$, and $2.1 \times 10^7$. The mean transposition efficiency is the mean fraction of total colonies assayed that are His$^+$.

EXAMPLE 3

Splicing Is Not Required for Ty1-H3mHIS3AI Transposition But Is Required for Generation of a His$^+$ Phenotype To determine whether the intron was ever retained during retrotransposition, 24 Ura$^+$ colonies were selected after transposition induction of pGTy1-H3mHIS3AI, and 5 were His$^+$. After plasmid segregation, His$^+$ and His$^-$ colonies were analyzed by Southern blot analysis with a HIS 3 probe (Table 2). Spliced elements were identified as those that recreated the HIS3 Msc I site and lacked the intronic Xba I site in a Pvu II/Msc I or Pvu II/Xba I digest (FIG. 1). Elements lacking the HIS3Msc I site but retaining the intron Xba I site were scored as unspliced. Twenty of the 24 colonies analyzed contained genomic copies of the HIS3-marked element. Eighteen of these harbored between one and six copies of the unspliced TymHIS3AI element. The 5 His$^+$ colonies each contained one copy of the spliced Tym-HIS3 element. A mean number of 1.7 marked transposition events per colony was found and 5 of 40 (12.5%) transposed Ty elements had lost the intron. Transposition induction of cells containing pGTy1-H3-HIS3mAI resulted in 2.5 marked transpositions per isolate. All of these colonies were phenotypically His+, and all of the transposed TyHIS3mAI elements remained unspliced. The transposition frequencies of the Ty1-H3 derivatives marked with HIS3AI gene in both orientations were similar to the activity of the intron less pGTy1-H3mHIS3 element (Table 2) and to other marked pGTy1-H3 derivatives (Boeke, et al. Science (1988) 239:280–282; Garfinkel, et al. Genetics (1988) 120:95–108). These data indicate that the intron in either orientation does not inhibit transposition, but splicing is required for histidine prototrophy.

TABLE 2

| Plasmid | Mean Number of Marked Transposition Events Per Induced Cell | | |
|---|---|---|---|
| | No. Spliced Elements Per Genome | No. Unspliced Elements Per Genome | No. Total Elements Per Genome |
| pGTy1-H3mHIS3AI | 0.2 (5/24) | 1.5 (35/24) | 1.7 (40/24) |
| pGTy1-H3HIS3mAI | 0 (0/16) | 2.5 (40/16) | 2.5 (40/16) |
| pGTy1-H3mHIS3 | N/A | N/A | 1.3 (26/20) |

Plasmids were analyzed in yeast strain GRF167. The values given are the mean number of bands hybridizing to a HIS3 probe on the appropriate Southern blot of transposition-induced colonies. The numbers in parentheses are the total number of junction fragment bands divided by the number of randomly selected transposition-induced colonies analyzed. N/A, not applicable.

EXAMPLE 4

Transposition of Chromosomal TymHIS3AI Elements Can Be Detected Phenotypically

The ability to determine if transposition of individual chromosomal elements could be detected was provided by the above analysis. When several strains harboring unspliced TymHIS3AI elements but lacking the pGTy1-H3mHIS3AI plasmid were grown at 20° C. and then replica plated to SC-his medium at 30° C. His+ papillae appeared. In contrast, histidine prototrophs were not detected in strains harboring chromosomal TyHIS3mAI elements. The frequency of His+ reversion in several strains containing unspliced TymHIS3AI elements decreased more than 20-fold if the cells were grown at 30° C. or 36° C. relative to 20° C. and His+ reversion was reduced at least 100 times in isogenic spt3 derivatives of these strains (data not shown). The dependence of His+ reversion on known modulators of Ty1 transposition and on intron orientation strongly suggests that retrotransposition of genomic TymHIS3AI elements is being detected.

Figure 2:
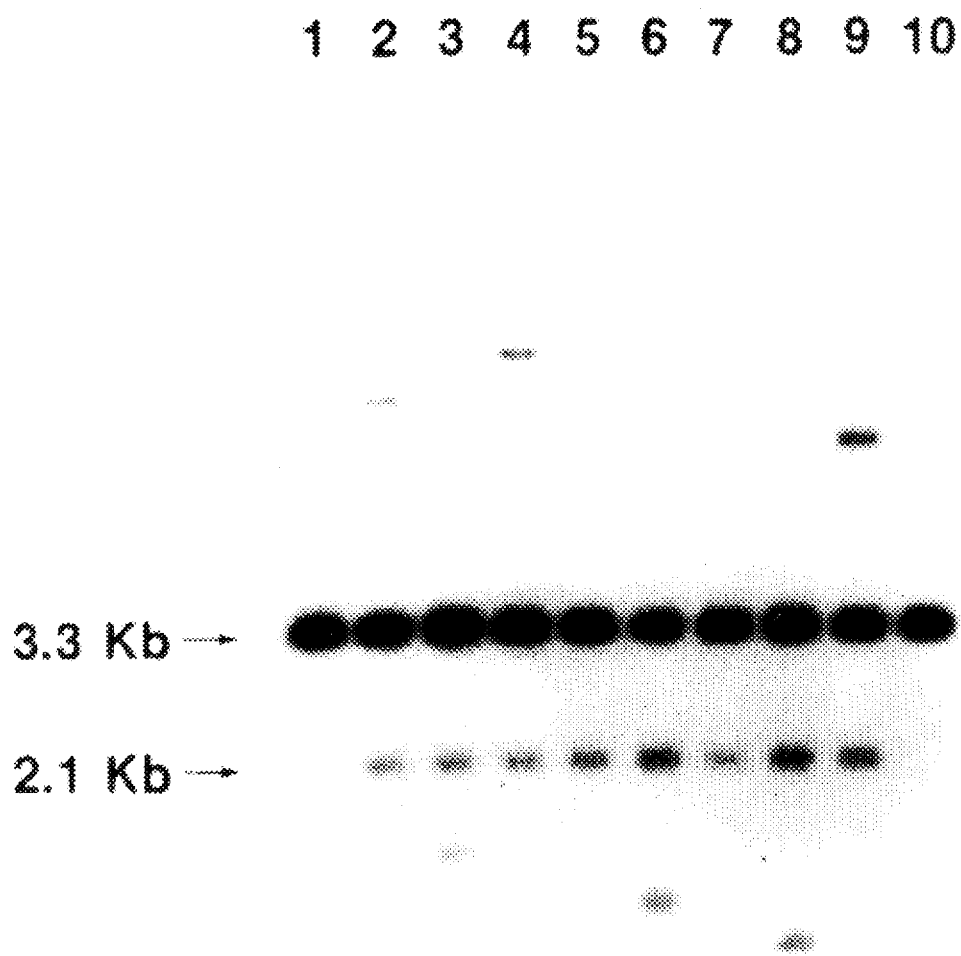
FIG. 2. Spontaneous His$^+$ revertants of a strain harboring the chromosomal TymHIS3AI element contain dispersed copies of Tym-HIS3 with the intron precisely removed. Parental strain JC242 (lanes 1 and 10) and eight His$^+$ revertants derived from strain JC242 (lanes 2–9) are shown. DNA from each revertant strain was digested with Pvu II and Msc I and probed with HIS3. The 3.3-kb band is the junction fragment between the 3' end of the TymHIS3AI element and flanking sequence DNA. The 2.1-kb band is an internal fragment of Tym-HIS3 from the Pvu II site in Ty1 to the Msc I site in the spliced HIS3 gene. The dispersed bands are junction fragments between the HIS3 Msc I site and a site in 3' flanking sequence DNA.

To extend these observations, strain JC242, a His⁻ strain harboring one unspliced TymHIS3AI element, was used to generate eight His+ revertants. DNA from these strains was digested with Pvu II and Msc I and then analyzed by Southern blot hybridization using a HIS3 probe (FIG. 2). The parental strain contains one 3.3-kilobase (kb) band because of the absence of an Msc I site in the unspliced HIS3AI gene. In the His+ revertants, this 3.3-kb band appears unaltered, suggesting that the His+ phenotype does not result from rearrangement of the HIS3AI gene within the original marked Ty1 element. However, the His+ colonies contain two new bands indicative of replicative transposition. In every case, a 2.1-kb band expected of an internal fragment from the Pvu II site in Ty1 to the Msc I site of the HIS3 gene is seen. The Msc I site within the HIS3 gene demonstrates that precise splicing has occurred in the process of TymHIS3 retrotransposition. Each His+ revertant also contains one other band of varied size. These bands represent junction fragments extending from the Msc I site in HIS3 to the next Pvu II or Msc I site in flanking sequences and are also suggestive of de novo transposition.

EXAMPLE 5

Rate of Transposition of Single Genomic Ty Elements

The His+ reversion rate was calculated by the method of Lea and Coulson (*J. Genet.* (1949) 49:264–285) for four strains containing either one, two, or five to six genomic copies of the TymHIS3AI elements (Table 3). The rate of His+ reversion in these strains varies between $3.4 \times 10^{-9}$ and $1.5 \times 10^{-7}$ per generation per TymHIS3AI element present in the genome. To estimate the average rate of Ty transposition, the His+ reversion rates were converted to transposition rates by accounting for the splicing efficiency and the effects of the marker gene on transposition. Our estimate is based on the assumption that genomic TymHIS3AI transcripts are spliced at the same frequency as those from the pGTy plasmid (Table 2). Therefore, about one-eighth of the transposition events are detected as histidine prototrophs. To determine if the presence of the HIS3AI gene decreased the level of Ty1 transposition, the abilities of the unmarked pGTy1-H3 and the pGTy1-H3mHIS3AI elements to transpose in an spt3 mutant DG789 were compared (Table 4). These results suggest that the marker gene lowers the level of Ty transposition by a factor of 11. Therefore, the average His+ reversion rate was multiplied by a factor of 88 to obtain an estimated transposition rate of $3 \times 10^{-7}$ and $1 \times 10^{-5}$ transposition events per Ty1 element per generation.

To determine whether the 50-fold variation in transposition rates might result from differences in transcript levels of individual TymHIS3AI elements, Northern blot hybridizations (FIG. 3) with total RNA from low and high-reverting strains JC234 (lane 1) and JC242 (lane 2) were performed. The results show that although the amount of total Ty RNA is similar, the level of TymHIS3AI RNA is much lower in strain JC234 than JC242.

TABLE 3

| | Rate of His+ Reversion In Yeast Strains Containing Genomic TymHIS3AI Elements | | |
|---|---|---|---|
| Strain | No. of TymHIS3AI Elements | Rate of His+ Reversion ($\times 10^{-7}$) | 22 Mean Rate Per TymHIS3AI Element ($\times 10^{-7}$) |
| JC234 | 1 | 1.034 ± 0.029 | 0.034 |
| JC242 | 1 | 1.6 ± 0.5 | 1.6 |
| JC246 | 2 | 1.4 ± 0.2 | 0.7 |
| JC271 | 5–6 | 9.1 ± 3.2 | 1.5–1.8 |

Ura⁻His+ colonies isolated after transposition induction of plasmid, pGTy1-H3mHIS3AI in strain GRF167. The number of TymHIS3AI elements was determined by Southern blot analysis. The rate of His+ reversion is expressed as mutations per cell per generation (means=95% confidence interval).

TABLE 4

Relative Transposition Levels of pGTy1-H3 and
pGTy1-H3mHIS3AI in spt3 Mutant DG789

| Plasmid | No. of New Bands Hybridizing to a Ty1 Probe | No. of Colonies Tested | Mean no. of Transposition Events |
| --- | --- | --- | --- |
| pGTy1-H3 | 40 | 16 | 3.5 |
| pGTy1-H3mHIS3AI | 3 | 13 | 0.23 |

EXAMPLE 6

Single-Step Assay for Retrotransposition

Figure 4:
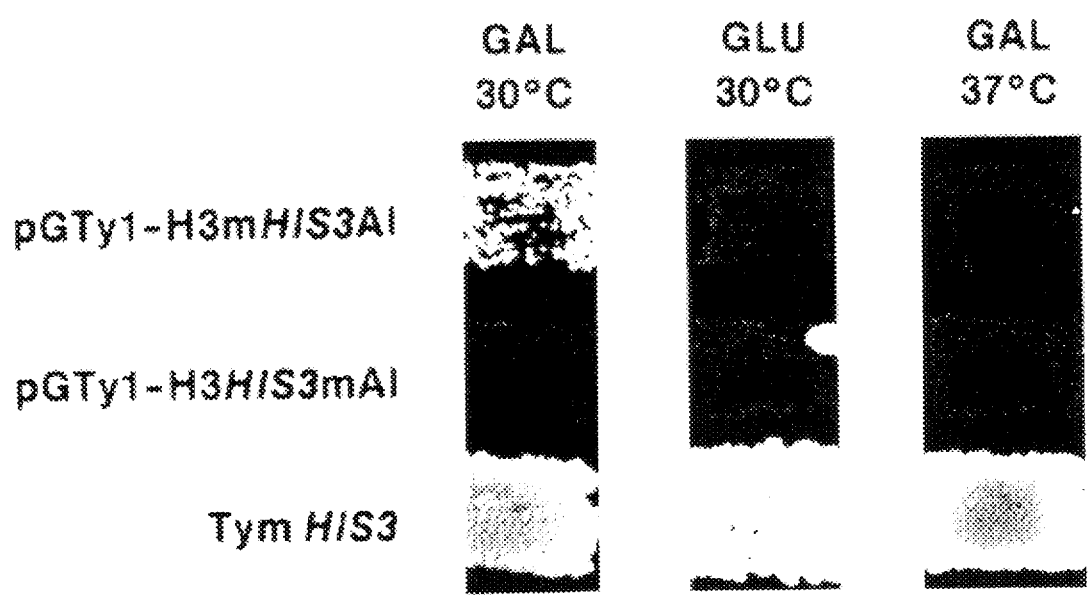
FIG. 4. Single-step assay for transposition of Ty1 marked with the retrotransposition reporter gene. Strains containing pGTy1-H3 marked with HIS3AI in the spliceable (pGTy1-3mHIS3AI) or unspliceable (pGTy1-H3HISmAI) orientation or a chromosomal copy of TymHIS3 were replica plated onto SC-ura galactose (Gal) or glucose (Glu) plates containing limiting mounts of histidine (0.3 µM) and grown at 30° C. or37° C.

Another application of the HIS3AI reporter gene is in its use in a single-step test for chemical agents or conditions that effect retrotransposition. A single-step test was developed by replica plating cells containing pGTy1-H3mHIS3AI onto Sc-ura galactose plates that contain limiting amounts of histidine (FIG. 4). These plates select for maintenance of the plasmid and induce transcription of the marked element. However, growth of the cells beyond a few generations cannot occur unless they become His+ by transposition of the spliced TymHIS3 element. Induction of the pGTy1-H3mHIS3AI transcription in limiting histidine medium results in a large number of histidine prototrophs. As expected, repressing pGTy1-H3mHIS3AI, transcription by plating on glucose blocks growth because there is no transposition of the marked element.

Figure 3:
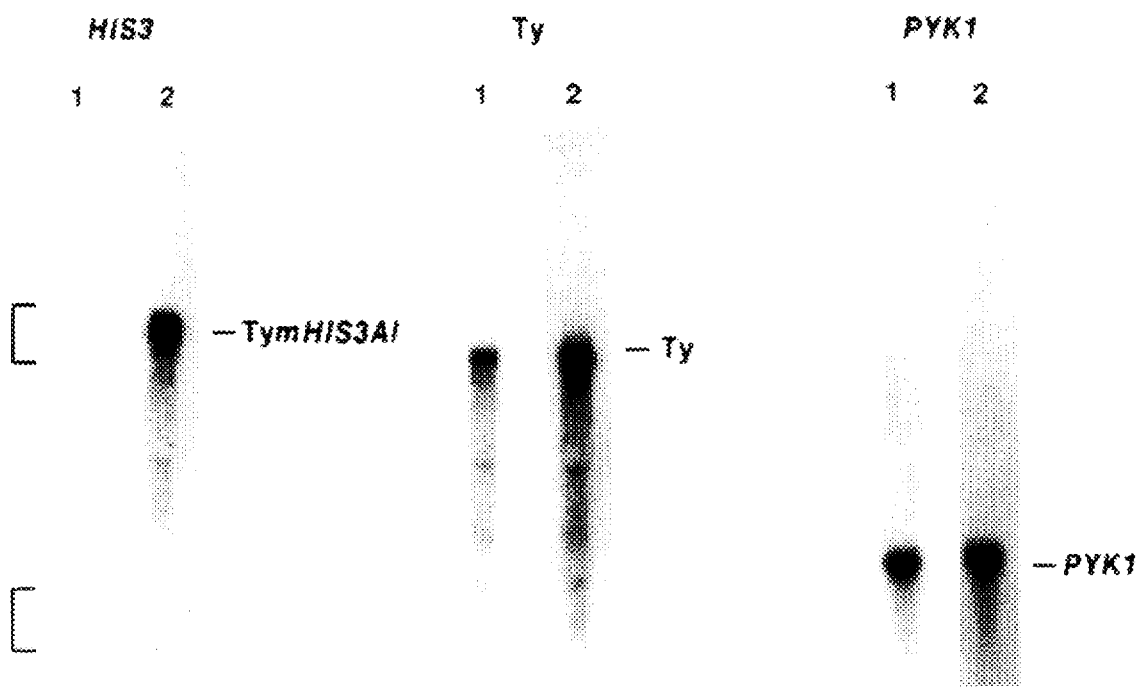
FIG. 3. Northern blot analysis of two strains each containing a single genomic TymHIS3AI element. A Northern blot containing a single genomic TymHIS3AI element. A Northern blot containing 5 µg of total RNA from strains JC234 (lane 1) and JC 242 (lane 2) was sequentially hybridized with HIS3, Ty1, and PYK1 probes. A longer exposure of the bracketed region of lane 1, required to detect the TymHIS3AI transcript in strain JC234, is shown below in lane1.

To determine whether the single-step retrotransposition test could be used to demonstrate the inhibition of transposition, induction of pGTy1-H3mHIS3AI was compared at semipermissive (30° C.) or nonpermissive (37° C.) temperatures (Paquin, C. E., et al. Science (1984) 224:53–55; D.J.G., unpublished results). As shown in FIG. 3, no His+ revertants resulted from galactose induction of the pGTy1-H3mHIS3 element at 37° C. This is not due to temperature-dependent expression of the HIS3 gene, since a strain containing a transposed copy of TymHIS3 grew well at 37° C.

EXAMPLE 7

Detection of Retrotransposition Inhibitors

The above-described assay was used to show that the antineoplastic agent hydroxyurea markedly inhibits Ty transposition (FIG. 5). The zone of inhibition surrounding the area of where hydroxyurea was applied is dependent on the presence of histidine in the medium (FIG. 5, plate A). The absence of a zone of inhibition on plates containing histidine indicates that hydroxyurea does not markedly inhibit growth of the yeast cells under the conditions used in this experiment (FIG. 5, plate B).

EXAMPLE 8

Construction of pHART21

Figure 7:
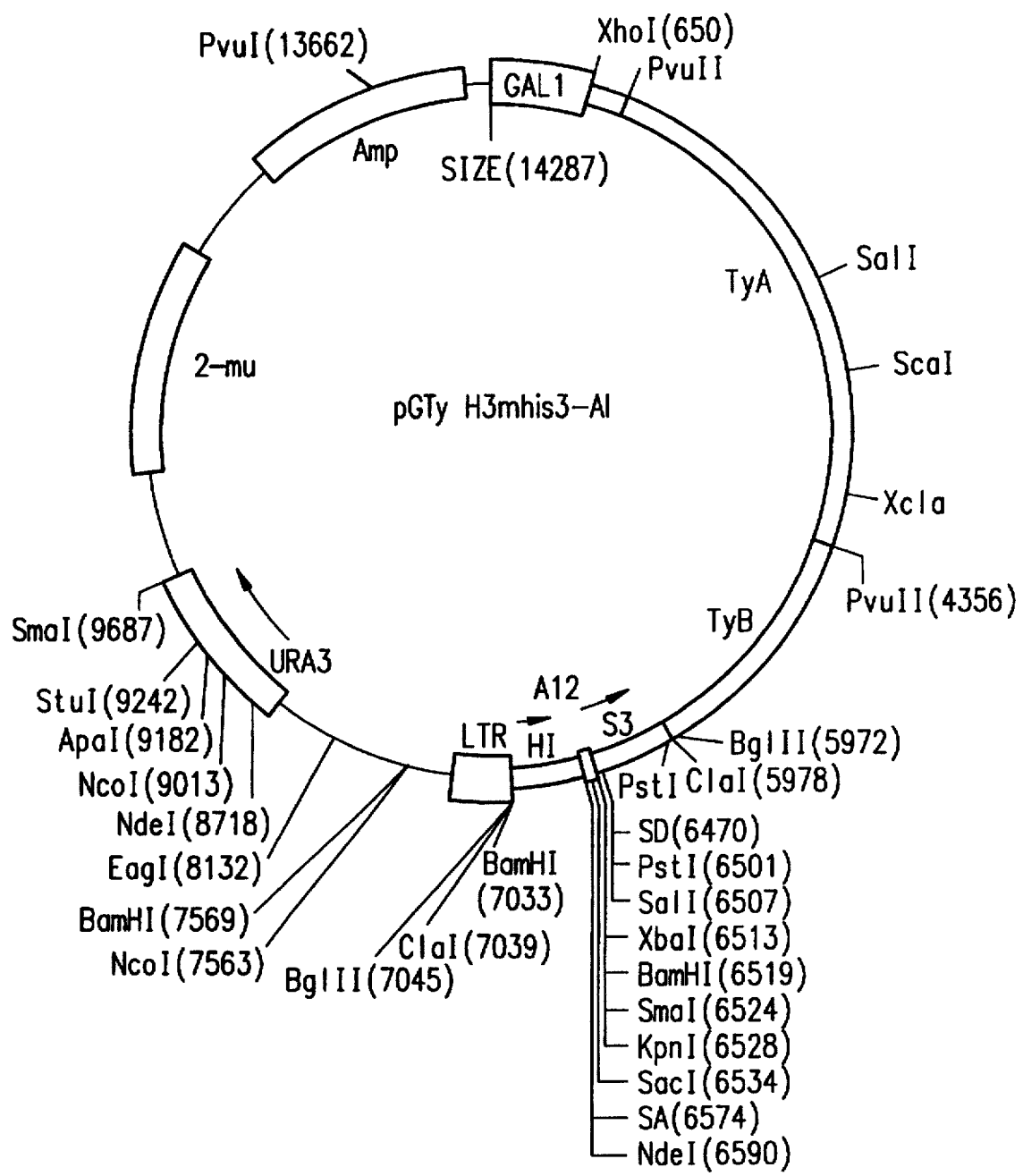
FIG. 7. pGTyH3mhis3-AI. The abbreviations used are: GAL1, yeast GAL1 promoter; 2-µm, yeast 2 µm origin of replication; URA3, yeast URA3 gene; Amp, ampicillin resistance gene; TyA, Ty1 element TyA; TyB, Ty1 element TyB;HIS3, yeast HIS3 gene having a yeast artificial intron, AI, inserted in antisense orientation relative to HIS3 transcription; SD, splice donor; SA, splice acceptor.
Figure 8:
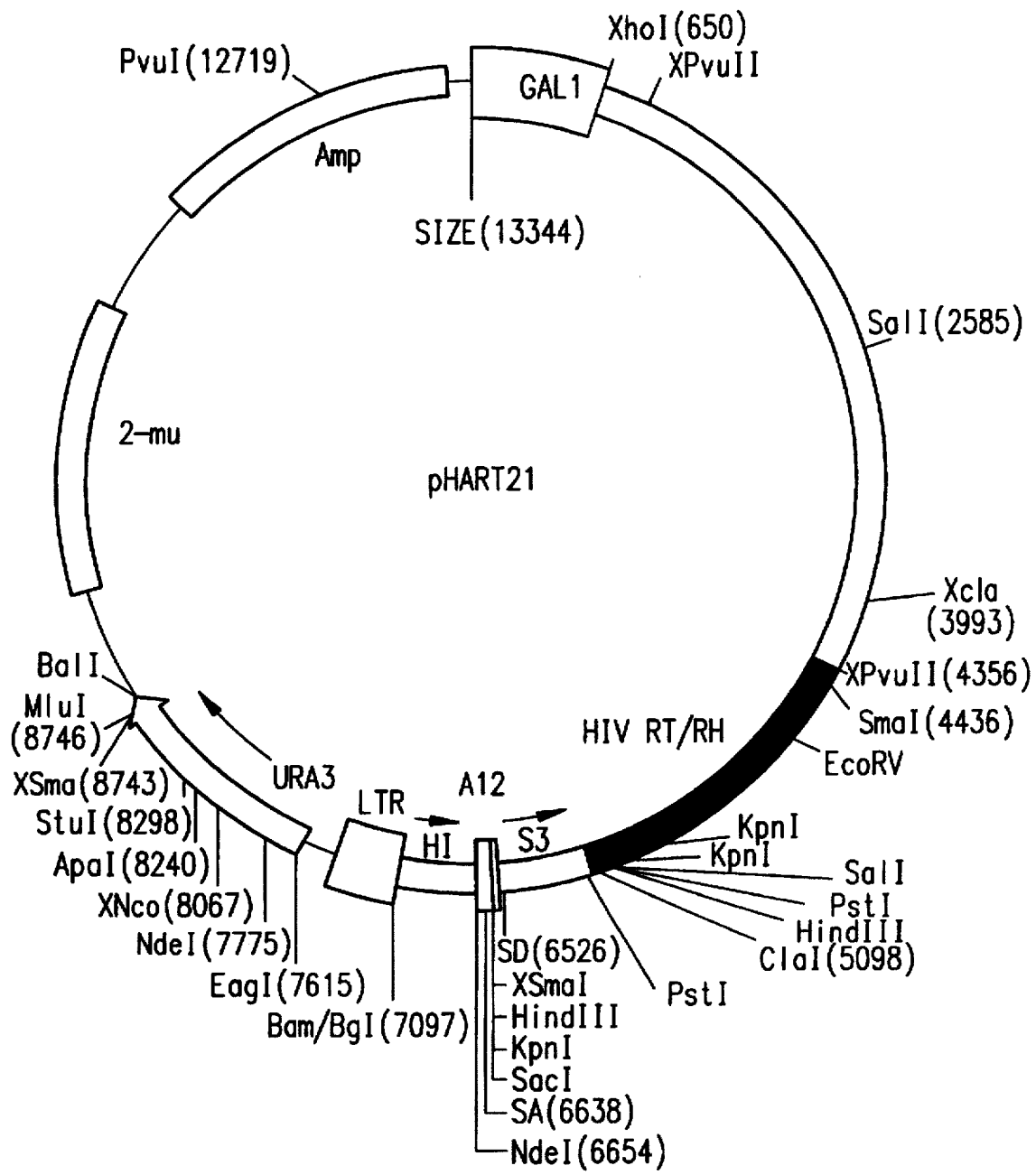
FIG. 8. pHART 21. Abbreviations same as in FIG. 7; an "X" prefix to a restriction enzyme recognition site indicates a site that was present in pGTy H3mhis3-AI that has been destroyed in the construction of pHART21; HIV RT/RH, HIV-1 RT/RH gene.

The plasmid pHART21 (FIG. 8) has two features that distinguish it from the pGTy-H3mhis3-AI plasmid (FIG. 7). First is the substitution of HIV-1 RT/RH for the Ty RT/RH. Second, the vector has been modified slightly to facilitate the insertion of variant HIV-RT/RH sequences or the coding regions of other reverse transcriptases.

The plasmid pHART21 was configured such that subsequent cloning of mutant HIV-1 RT/RH derivatives can be performed utilizing a unique SmaI site at HIV-1 RT/RH codon 15 and a unique ClaI site adjacent to the HIV-1 RT/RH C-terminus.

Figure 9:
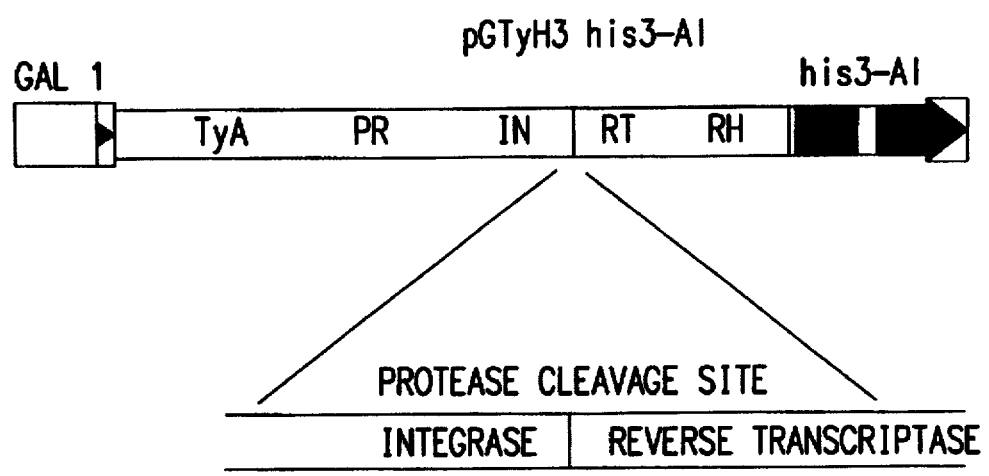
FIG. 9. Fusion of the HIV-1 RT ORF to the Ty ORF. Abbreviations used are: GAL 1, yeast GAL 1 promoter; TyA, Ty1 element TyA; PR, yeast Ty1 protease coding sequences; IN, yeast Ty1 integrase coding sequences; RT/RH, yeast Ty1 reverse transcriptase RT/RH coding sequences; his3-AI, yeast HIS3 gene having a yeast artificial intron in antisense orientation to HIS3 transcription; HIV-RT, RH, HIV-1 RT/RH coding sequences. The boxed arrow heads represent the Ty1 long terminal repeats and the direction of Ty1 transcription.
Figure 9:
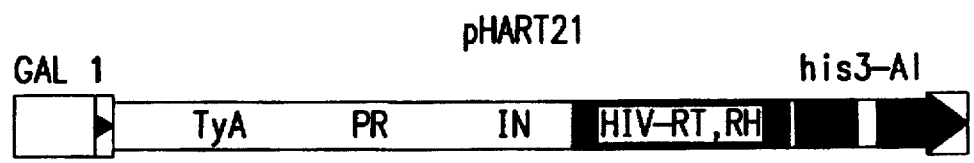

The fusion of the HIV-RT ORF to the Ty ORF was done at a PvuII site near the codons for the natural site of cleavage by the Ty protease between Ty integrase (IN) and Ty RT (FIG. 9; SEQ ID NO: 1(nucleic acid) and SEQ ID NO: 2(polypeptide)). The sequence from the exPvuII site to the SmaI site at codon 15 of HIV-1 RT/RH are derived from a PCR product. The remainder of the HIV-1 RT/RH sequence was isolated as a SmaI-ClaI fragment from a clone obtained from Dr. Stephen Hughes (Hizi, A., Mc Gill, C. and Hughes, S. H., Proc. Natl. Acad. Sci. 85 (1988) 1218–1222).

Five alterations to the pGTy-H3mhis3-AI vector were made to facilitate the expression of exogenous reverse transcriptase genes as Ty fusions: 1) We used a variant of Ty1 that does not have the PvuII site in TyA near the GAL1 promoter. 2) The SmaI site near the end of the URA3 gene was destroyed by digesting with SmaI and ligating in a MluI linker. 3) A slightly altered form of the artificial intron (AI2) was used in which the PstI, SalI, XbaI, and BamHi sites have been removed by single base changes and the SmaI site was destroyed by digesting with SmaI and ligating in a HindIII linker. 4) A URA3 gene with a single base change that destroys the NcoI site was substituted into the vector deleting the region from the NcoI site (changed to an EagI site) distal of the 3'LTR to the start of the URA3 sequences. 5) The ClaI site between the his3AI2 gene and the LTR was removed by ligating the adjacent BamHI and BglII sites.

The Ty1 RT/RH domain was replaced with the HIV-1 RT/RH domain initially using PCR-cloning to create plasmid pHART1. The junction between Ty1 integrase C-terminal coding sequence and N-terminal HIV-1 RT/RH coding sequence was made such that a Ty1 PvuII site was removed by blunt-end ligation to the Ecl136H site of a PCR-generated HIV-1 RT/RH segment (HIV-1 isolate HXB2). An additional leucine codon (CTA) was added due to the presence of the Ecl136II site. The leucine codon is followed by the Ty1 RT/RH codons for lysine (AAA), alanine (GCA), valine (GTA), and then the HIV-1 RT/RH N-terminal proline codon (CCC) (FIG. 9; SEQ ID NO: 3(nucleic acid) and SEQ ID NO: 4(polypeptide)). A ClaI site was added adjacent to the C-terminus of HIV-1 RT/RH for subsequent ligation to the modified pGTy1-H3mhis3-AI expression plasmid described above.

Molecular clones of either wildtype, RT−, or RH− HIV-1 RT/RH segments were used to replace the pHART1 HIV-1 RT/RH segment to create pHART21, pHART22, and pHART23, respectively. In the resulting vector pHART21, the SmaI site at codon 15 in the HIV-1 RT/RH clone and the ClaI site between the HIV sequences and the his3-AI indicator gene are unique. HIV-1 RT/RH sequences from RT defective and RH defective mutants (provided by Dr. Stephen Hughes (Boyer, P. L., Ferris, A. L. and Hughes, S. H. J. Virol. 66 (1992) 1031–1039; Boyer, P. L., et al. J. Mol. Biol. 243 (1994) 472–483)) were substituted as SmaI-ClaI fragments to generate pHART22 and pHART23 respectively. Initial experiments were performed with pHART1, a plasmid with a similar HIV-1 RT/RH substitution and the altered artificial intron (still containing the SmaI site), but without the other changes to the vector.

EXAMPLE 9

Assay for Rate of His+ Formation by HART Plasmids

This example hybrid Ty1-H3mhis3-AI retrotransposon contains the HIV-1 RT/RH gene domain in place of the Ty1

RT/RH domain. The hybrid element, HART21, is expressed from a plasmid-borne GAL1 promoter carried on a multi-copy plasmid in yeast cells where the level of endogenous RT/RH activity is minimized by mutation of the cellular spt3 gene. The HART21 assay is similar in all other respects to the pGTy1-H3mhis-3-AI transposon assay also described herein. Cells containing pHART21 give rise to many $His^+$ derivatives when galactose-induced, which is comparable to the efficiency of $His^+$ formation observed with pGTy1-H3mhis3-AI (Table 5).

The HART21 system differs from Ty1 mhis3-AI in an important respect. The $His^+$ events obtained with HART21 do not result from retrotransposition, but from a related process called cDNA-mediated recombination. cDNA recombination predominates when reverse transcription products do not undergo transpositional integration catalyzed by the Ty1-encoded enzyme integrase. HART21 cDNA undergoes homologous recombination with endogenous Ty elements residing in the yeast genome. However, the $His^+$ cDNA recombination events are completely dependent on functional HIV-1RT/RH (Table 5) and, therefore, serve as a faithful biological indicator of HIV-1 RT/RH activities in yeast. In addition, the present assay demands that HIV-1 RT act as a RNA-dependent DNA polymerase and ribonuclease H, activities that are unique to this type of enzyme and a major reason for choosing RT/RH as a target for drug intervention.

TABLE 5

| HIV-1 RT/RH-Mediated $His^+$ Formation | | |
|---|---|---|
| Plasmid | HIV-1 RT/RH | Rate of $His^+$ Formation |
| HART21 | Wildtype | $1.7 \times 10^{-3}$ |
| HART22 | $RT^-$ | $\leq 1.5 \times 10^{-5}$ |
| HART23 | $RH^-$ | $\leq 1.2 \times 10^{-5}$ |

Each measurement represents the average of four cultures. The total number of colony-forming units was similar in each set of cultures. The rate of $His^+$ formation is the number of $His^+$ events/cell/generation. The HART21, HART22 and HART23 plasmids are similar, except HART22 and HART23 contain missense mutations in the RT and RH domains, respectively.

EXAMPLE 10

Analysis of Homologous Recombination Events

To determine whether HART 21 was producing $His^+$ cells by cDNA-mediated homologous recombination or by transposition, it was determined whether HART 21 inserted into the host chromosome only, indicating retrotransposition, or into both the chromosome and the plasmid, indicating homologous recombination, by standard methods (Derr, et al. Cell (1991) 67:355–364; Sharon, et al. Mol. Cell. Biol. (1994) 14:6540–6551).

EXAMPLE 11

Detection of Reverse Transcriptase/RNase H Inhibitors

This example is similar to those outlined in Examples 6 and 7. Cells containing an spt3 mutation and HART21 were spread onto SC-uracil galactose plates containing 100 microliters of a 2M hydroxyurea solution (200 μm) spotted onto a sterile filter placed in the center of the plate. After incubation at 20° C. for five days, the plates were replica-plated to the following media, incubated at 30° C. and photographed (FIG. 6): Panel A, SC-histidine+hydroxyurea-uracil plate to detect inhibition of $His^+$ formation by continued presence of hydroxyurea; Panel B, SC+histidine+hydroxyurea-uracil plate to detect general inhibition of growth by hydroxyurea; Panel C, SC-histidine-hydroxyurea-uracil to show the level of $His^+$ colony formation in the absence of hydroxyurea. These results show that hydroxyurea inhibits HIV-1-mediated $His^+$ formation in yeast.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A vector comprising a selectable marker gene inserted into a retrotransposon, wherein the retrotransposon comprises a retroviral reverse transcriptase/RNase H gene domain and wherein the selectable marker gene contains an intron inserted into a coding sequence of the marker gene and the intron is in antisense orientation relative to transcription of the marker gene and in sense orientation relative to transcription of the retrotransposon.

2. The vector of claim 1, wherein the retrotransposon is a yeast Ty element.

3. The vector of claim 1, wherein the reverse transcriptase/RNase H gene domain is an HIV-1 reverse transcriptase/RNAse H gene domain.

4. The vector of claim 1, wherein the reverse transcriptase/RNase H gene domain is an HIV-2 reverse transcriptase/RNAse H gene domain.

5. The vector of claim 1, wherein the reverse transcriptase/RNase H gene domain is a feline immunodeficiency virus reverse transcriptase/RNAse H gene domain.

6. The vector of claim 1, wherein the reverse transcriptase/RNAse H gene domain is an avian immunodeficiency virus reverse transcriptase/RNAse H gene domain.

7. The vector of claim 1, wherein the reverse transcriptase/RNase H gene domain is selected from the group consisting of a HIV-2, simian immunodeficiency virus, bovine immunodeficiency virus, and equine infectious anemia virus.

8. The vector of claim 1, wherein the retrotransposon is under transcriptional control of an inducible promoter.

9. The vector of claim 1, wherein the selectable marker gene is a yeast HIS3 gene.

10. The vector of claim 1, wherein the intron is a yeast artificial intron.

11. A cell transformed with the vector of claim 1.

12. The vector of claim 2, wherein the retrotransposon is Ty1.

13. A cell transformed with the vector of claim 3.

14. A cell transformed with the vector of claim 4.

15. The vector of claim 8, wherein the inducible promoter is GAL1 promoter.

16. A method of screening for a compound with the ability to inhibit retroviral replication comprising
    (a) contacting the cell of claim 11 with the compound,
    (b) culturing the cell in selective media and
    (c) detecting inhibition of growth of the cell, a compound that inhibits growth of the cell being a compound that inhibits retroviral replication.

17. A method of screening for a compound with the ability to inhibit reverse transcriptase comprising
    (a) contacting the cell of claim 11 with the compound,
    (b) culturing the cell in selective media and
    (c) detecting inhibition of growth of the cell, a compound that inhibits growth of the cell being a compound that inhibits reverse transcriptase.

18. A method of screening for a compound with the ability to inhibit HIV-1 replication comprising
    (a) contacting the cell of claim 13 with the compound,
    (b) culturing the cell in selective media and (c) detecting inhibition of growth of the cell, a compound that inhibits growth of the cell being a compound that inhibits HIV-1 replication.

19. A method of screening for a compound with the ability to inhibit HIV-2 replication comprising
   (a) contacting the cell of claim 14 with the compound,
   (b) culturing the cell in selective media and
   (c) detecting inhibition of growth of the cell, a compound that inhibits growth of the cell being a compound that inhibits HIV-2 replication.

20. A method of screening for a compound with ability to inhibit retroviral replication comprising
   (a) culturing a cell that is transformed with a vector comprising a DNA segment comprising a selectable marker gene inserted into a retrotransposon wherein the selectable marker gene contains an intron inserted into a coding sequence of the gene and the intron is present in an antisense orientation relative to transcription of the marker gene and in a sense orientation relative to transcription of the retrotransposon, in selective media,
   (b) contacting the cell with the compound, and
   (c) detecting inhibition of growth of the cell, a compound that inhibits growth of the cell being a compound that inhibits retroviral replication.

21. A method of screening for a compound with ability to inhibit retrotransposition comprising
   (a) culturing a cell that is transformed with a vector comprising a DNA segment comprising a selectable marker gene inserted into a retrotransposon wherein the selectable marker gene contains an intron inserted into a coding sequence of the gene and the intron is present in an antisense orientation relative to transcription of the marker gene and in a sense orientation relative to transcription of the retrotransposon, in selective media,
   (b) contacting the cell with the compound, and
   (c) detecting inhibition of growth of the cell, a compound that inhibits growth of the cell being a compound that inhibits retrotransposition.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:1:

ATTCACCTGA TTGCAGCTGT AAAAGCAGTA AAA        3 3

( 2 ) INFORMATION FOR SEQ ID NO:2:

( i ) SEQUENCE CHARACTERISTICS:
        ( A ) LENGTH: 11 amino acids

```
            ( B ) TYPE: amino acid
            ( C ) STRANDEDNESS: Not Relevant
            ( D ) TOPOLOGY: linear ( i i ) MOLECULE TYPE: peptide ( x i ) SEQUENCE DESCRIPTION: SEQ ID NO:2:

Ile His Leu Ile Ala Ala Val Lys Ala Val Lys
    1               5                   10

( 2 ) INFORMATION FOR SEQ ID NO:3:

( i ) SEQUENCE CHARACTERISTICS:
            ( A ) LENGTH: 45 base pairs
            ( B ) TYPE: nucleic acid
            ( C ) STRANDEDNESS: double
            ( D ) TOPOLOGY: linear ( i i ) MOLECULE TYPE: other nucleic acid ( x i ) SEQUENCE DESCRIPTION: SEQ ID NO:3:

ATTCACCTGA  TTGCAGCTCT  AAAAGCAGTA  CCCATTAGCC  CTATT                                45

( 2 ) INFORMATION FOR SEQ ID NO:4:

( i ) SEQUENCE CHARACTERISTICS:
            ( A ) LENGTH: 15 amino acids
            ( B ) TYPE: amino acid
            ( C ) STRANDEDNESS: Not Relevant
            ( D ) TOPOLOGY: linear ( i i ) MOLECULE TYPE: peptide ( x i ) SEQUENCE DESCRIPTION: SEQ ID NO:4:

Ile His Leu Ile Ala Ala Leu Lys Ala Val Pro Ile Ser Pro Ile
    1               5                   10                  15
```